US008211675B2

(12) United States Patent (10) Patent No.: US 8,211,675 B2
Visser et al. (45) Date of Patent: Jul. 3, 2012

(54) LACTIC ACID PRODUCTION FROM CONCENTRATED RAW SUGAR BEET JUICE

(75) Inventors: Diana Visser, Gorinchem (NL); Jan Van Breugel, Woudrichem (NL); Johannes Martinus De Bruijn, Peterborough (GB); Paul A'Campo, Eemnes (NL)

(73) Assignee: Purac Biochem BV, Gorinchem (NL)

( * ) Notice: Subject to any disclaimer, the term of this patent is extended or adjusted under 35 U.S.C. 154(b) by 646 days.

(21) Appl. No.: 12/308,464

(22) PCT Filed: Jun. 22, 2007

(86) PCT No.: PCT/EP2007/056256
§ 371 (c)(1),
(2), (4) Date: Jan. 29, 2009

(87) PCT Pub. No.: WO2008/000699
PCT Pub. Date: Jan. 3, 2008

(65) Prior Publication Data
US 2010/0062503 A1 Mar. 11, 2010

(30) Foreign Application Priority Data
Jun. 22, 2006 (EP) ..................................... 06115885

(51) Int. Cl.
*C12P 7/56* (2006.01)
(52) U.S. Cl. ...................... 435/139; 435/170; 435/252.9
(58) Field of Classification Search .................. 324/139, 324/170, 252.9
See application file for complete search history.

(56) References Cited

U.S. PATENT DOCUMENTS

| 1,969,237 | A |   | 8/1934  | Ricard et al. |        |
|-----------|---|---|---------|---------------|--------|
| 4,523,959 | A | * | 6/1985  | Exertier      | 127/46.2 |
| 6,440,222 | B1|   | 8/2002  | Donovan et al.|        |
| 6,936,290 | B2| * | 8/2005  | Swain et al.  | 426/48 |
| 2001/0054420 | A1 | * | 12/2001 | Reisig et al. | 127/55 |

FOREIGN PATENT DOCUMENTS

WO  WO 00/56912 A1  9/2000
WO  WO 2006/001034 A2  1/2006

OTHER PUBLICATIONS

Young et al. Lebensm.—Wiss. u.—Technol. (2005) 38: 73-75.*
Grabka, J. "Production of Saccharides" in "Chemical and Functional Properties of Food Saccharides" Ed: P. Tomasik. Chapter 4 10 pages CRC Press.*
El-Sherbiny et al., "Utilization of Beet Molasses in the Production of Lactic Acid," Egyptian Journal of Food and Science, vol. 14, No. 1, 1986, pp. 91-100.
Kotzamanidis et al., "Optimization of Lactic Acid Production From Beet Molasses by *Lactobacillus delbrueckii* NCIMB 8130," World Journal of Microbiology & Biotechnology, vol. 18, No. 5, 2002, pp. 441-448.

K. Antal, "The Manufacture of Alcohol From Sugar Beets," Zeitschrift Fur Spiritusindustrie, vol. 34, No. 239-40, 1911, pp. 252-253.
Austmeyer et al., "Combined Production of Ethanol and White Sugar," Zuckerindustrie, vol. 113, No. 9, 1988, 765-772.
Bonelli et al., "Industrial Preparation of Lactic Acid From Sugar Beet," Pontelagoscuro, Jul. 1918, pp. 1-8.
Zakharov et al. "Production of Lactic Acid From Sugar Beet and Cases of Inactivation of Lactic Acid Fermentation," Mikrobiologiya, vol. 15, No. 1. 1946. (English translation).
Zakharov et al., "Production of Lactic Acid From Sugar-Beet and Cases of Inactivation of Lactic Acid Fermentation," Mikrobiologiya, vol. 15, No. 1, 1946, pp. 1-10.
Hollaus et al., "Experimental Studies on Bacterial Degradation of Sugar in Raw Juice and in Preliming Juice," Sucrerie Belge, vol. 99, No. 5, 1980, pp. 183-193.
Bonelli et al., "The Industrial Preparation of Lactic Acid From Sugar Beets," Ind. Chim. Min. Met. (1918) vol. 5, pp. 121-124.
Manzke et al., "Raw Thick Juice: Manufacture, Storage and Utilization as Feedstock in the Biotechnological Industry," Zuckerindustrie, vol. 117, No. 12, 1992, pp. 984-990.
Goeksungur et al., "Batch and Continuous Production of Lactic Acid From Beet Molasses by *Lactobacillus delbrueckii* IFO 3202," Journal of Chemical Technology and Biotechnology, vol. 69, No. 4, Aug. 1, 1997, pp. 399-404.
Goeksungur et al., "Production of Lactic Acid From Beet Molasses by Calcium Alginate Immobilized *Lactobacillus delbrueckii* IFO 3202," Journal of Chemical Technology and Biotechnology, vol. 74, No. 2, Feb. 1999, pp. 131-136.
Monteagudo et al., "Kinetics of Lactic Acid Fermentation by *Lactobacillus delbrueckii* Grown on Beet Molasses," Journal of Chemical Technology and Biotechnology, vol. 68, No. 3, Mar. 1, 1997, pp. 271-276. Monteagudo et al., "Optimization of the Conditions of the Fermentation of Beet Molasses to Lactic Acid by *Lactobacillus delbrueckii*," Acta Biotechnologica, vol. 14, No. 3, 1994, pp. 251-260.

* cited by examiner

*Primary Examiner* — Susan Hanley
(74) *Attorney, Agent, or Firm* — Oliff & Berridge, PLC

(57) ABSTRACT

The present invention is in the field of the preparation of lactic acid by means of fermentation on industrial scale wherein a concentrated raw beet juice having a Brix of at least 60 is used as fermentation substrate. After dilution to the desired initial sugar concentration and addition of nutrients, the juice is fermented to lactic acid and/or lactate by means of a lactic acid-producing microorganism. Said concentrated raw beet juice is prepared by: washing and cutting sugar beet and extracting the cossettes in water, removing the beet pulp from the resulting raw beet juice, and heat treating the raw beet juice at a temperature between 50 and 90 degrees Celsius, and concentrating the raw beet juice to at least 60 Brix.
It was found that concentrated beet juice having a Brix of at least 60 is storage-stable, is not very sensitive to infections, and can be used as fermentation substrate for lactic acid production on industrial scale with the same yield, chemical purity, optical purity, clarity and taste as lactic acid obtained from fermenting white sugar.

9 Claims, 1 Drawing Sheet

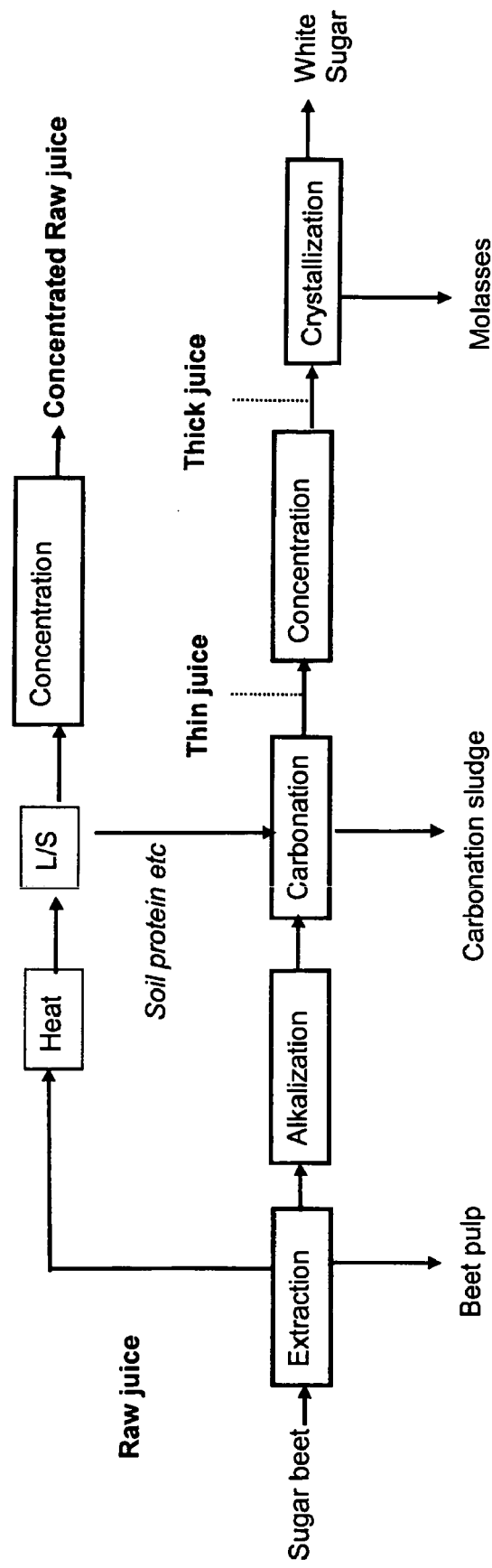

LACTIC ACID PRODUCTION FROM CONCENTRATED RAW SUGAR BEET JUICE

CROSS-REFERENCE TO RELATED APPLICATIONS

This Application is a national stage application of International Application No. PCT/EP2007/056256 filed on Jun. 22, 2007, which claims priority to European Patent Application No. 06115885.3 filed on Jun. 22, 2006.

BACKGROUND

Lactic acid, its salts and esters have long been used as food additive and in various chemical and pharmaceutical applications. More recently, lactic acid has been used in the making of biodegradable polymers both as a replacement for present plastic materials as well as various new uses where biodegradability is needed or desired such as for medical implants, solvable sutures and controlled release drugs. The production of lactic acid is commonly carried out by fermentation by means of a micro-organism such as bacteria, yeasts and fungi. The fermentation medium consists of a carbohydrate substrate together with suitable mineral and proteinaceous nutrients. A commonly used fermentation substrate is white sugar. Sugar is the most important contributor to the manufacturing cost price of lactic acid. Major reductions in the manufacturing cost price of lactic acid can therefore be accomplished if a less expensive carbohydrate source can be used than white sugar. To this end several research groups tried to ferment cheaper byproducts and intermediates of a sugar production plant to lactic acid. However, while the fermentation of these crude sugar sources to ethanol can be done readily, problems are encountered when trying to use these substrates on industrial scale for the fermentation to lactic acid. These problems lie in the field of fermentability, storage—stability, sensitivity to infections, the purification of the product of fermentation (i.e. the downstream processing) etcetera.

Examples of prior art wherein the fermentation of sugar beet juice to ethanol is described are *Raw thick juice: manufacture, storage and utilisation as feedstock in biotechnological industry*, G. Marke, P. V. Schmidt, R. Rieck, B. Senge, B. Steiner, Zuckerindustrie (1992), 117 (12), 984-90, *The manufacture of alcohol from sugar beets*, K. Antal, Zeitschrift fuer Spiritusindustrie (1911) 34, 239-40, 252-3 and *Combined production of ethanol and white sugar*, K. Austmeyer, H Roever, H. Zuckerindustrie (1988) 113 (9), 765-72.

The literature on fermentation of sugar beet juice to lactic acid on industrial scale is not so abundant.

For instance, in *The industrial preparation of lactic acid from sugar beets*, A. Bonelli, G. Gulinelli, Ind. Chim. Met. (1918), 5 121-4, the fermentation of raw sugar beet juice to lactic acid is described. This raw sugar beet juice only has a concentration of about 16 wt % sugar. First of all, as indicated in the publication this carbohydrate source is very sensitive to infections and often already infected to start with. This is confirmed in for instance, F. Hollaus et Al: *"Experimental studies on bacterial degradation in sugar of sugar in raw juice and preliming juice."* Sucrerie beige, vol 99, No 5, (1980), p. 183. With sugar beet factories running in campaigns and only active 3-4 months a year, it is clear that this provides storage problems. Secondly, with a concentration of only 16% the transport and storage costs will render this process relatively expensive. These factors make raw sugar beet juice unfit as a substrate for fermentation to lactic acid on an industrial scale.

In *Production of lactic acid from sugar beet and cases of inactivation of lactic acid fermentation*, I. P. Zakharov, M. F. Federova, Mikrobiologiya (1946), 15 (No. 1), 57-66, also the fermentation of raw sugar beet juice is described. Zakharov reports that the heating or sterilization of the sugar beet juice has a detrimental effect on the fermentation. The beet syrup, prepared by evaporation of beet juice to a sugar content of 51% was diluted and fermentation was tried: virtually no fermentation took place both with and without chalk (probably calcium hydroxide is meant here) addition. Zakharov concluded that a medium of such syrup proved unsuitable for the fermentation to lactic acid.

SUMMARY

All in all, it must be concluded that the fermentation of these crude substrates such as raw sugar beet juice to lactic acid on industrial scale proves to be much more complicated than a comparable fermentation to ethanol. The same can be said of the purification (i.e. the downstream processing) of lactic acid prepared by fermentation compared to the purification of fermentatively prepared ethanol.

We have found that concentrated raw beet juice having a Brix of at least 60 (i.e. amount of sugar in weight per 100 grams of liquid) is a suitable substrate for the fermentation on industrial scale to lactic acid and or lactate. Further, it appears to be storage-stable and is not very sensitive to infections. Furthermore, fermentation to lactic acid is achievable with the same yield, chemical purity, optical purity, clarity and taste as lactic acid obtained from fermenting sucrose, i.e. white sugar.

When processing sugar beet, the beet is usually washed with water, cut and the resulting cossettes are extracted with water, from which beet pulp is removed and the resulting raw juice is further processed to sugar by subsequent juice purification [i.e. traditionally by lime addition to a pH of approximately 11.2 in the pre-liming, followed by surplus lime addition in the main liming (the alkalization), addition of carbon dioxide in two subsequent stages (the carbonation), wherein after the first carbonation the carbonation sludge/lime is removed] resulting in thin juice, said thin juice is concentrated resulting in thick juice, said thick juice is subjected to one or more crystallization steps to form various sugar grades, and molasses as by-product.

The concentrated raw beet juice used in the process according to the invention is prepared by subjecting the raw juice (approximately 16% sugar) to a heating step at a temperature between 50 and 90° C. and concentrating the raw beet juice to a Brix of at least 60 (that is, without lime addition to a pH of approximately 11.2 and surplus lime addition followed by carbon dioxide addition in two stages with removal of carbonation sludge/lime). Optionally a liquid-solid separation step is performed between the heating step and the concentration step and/or after the concentration step to remove residual soil, small beet particles and protein. The concentration step is usually performed by evaporation at a temperature between 50 and 120° C. It is also possible to combine the heating and concentration step. If the heating and concentration steps are combined, the optional solid/liquid separation is conducted either prior to the heating/concentration or after. The concentrated raw beet juice can be added in diluted form to the fermentation. Usually the concentrated raw beet juice is diluted to a concentration of about 16-30 Brix, more preferably 20-30 Brix.

BRIEF DESCRIPTION OF THE DRAWINGS

FIG. 1 is a schematic diagram illustrating sugar beet processing and raw juice treatment for lactic acid fermentation.

The processing of sugar beet to white sugar and the preparation of concentrated raw beet juice from the raw beet juice which is an intermediate of the beet processing process is schematically illustrated by FIG. 1.

DETAILED DESCRIPTION

It was found that molasses and thick juice prepared during sugar beet processing is not very suitable for the fermentation to lactic acid on industrial scale. Without wishing to be bound to a theory we think that during the processing of the raw sugar beet juice to thick juice and further to molasses, several impurities are either concentrated in the molasses and/or thick juice or are introduced by reactions occurring during the alkalization, heat and carbon dioxide treatments (e.g. the results of Maillard reactions). Said impurities interfere with fermentation reactions to lactic acid on industrial scale. This is also shown in our experimental data. Sometimes the impurities can be removed by various pre-treatments, but this requires additional, laborious and expensive purification steps.

Goeksungur y et all: "*Batch and continuous production of lactic acid from beet molasses lactobacillus delbrueckii IFO 3202*" Journ. Chem. Techn. and Biotechn., vol 69, No. 4, (1997) pp. 399-404, and Goeksungur y et all: "*Production of lactic acid from beet molasses by calcium alginate immobilized lactobacillus delbrueckii IFO 3202*" Journ. Chem. Techn. and Biotechn., vol 74, No. 2, (1999) pp. 131-136, describe the production of lactic acid from pretreated beet molasses with specific bacteria. The pretreatment comprises acidification with sulphuric acid, boiling, centrifusion, filtration and clarification, including pasteurization. The experiments were conducted in 250 $cm^3$ and 500 $cm^3$ flasks and it was indicated that even with a low initial sugar concentration (28.2 g/l) the sugar was not completely utilized. The authors attribute that to the complex nature of molasses (i.e. impurities).

Monteagudo J. M. et Al: "*Kinetics of lactic acid fermentation by lactobacillus delbruekii grown on beet molasses*", Journ. Chem. Techn. And Biotechn., vol 68, No 3, (1997), pp 271-276 describes the experiments of lactic acid fermentation on beet molasses on lab scale (5 liter flasks). Here also the sugar was not completely utilised.

El Sherbiny et al: "*Utilisation of beet molasses in the production of lactic acid*", Egyptian Journ. Of Food SC. vol 14, No 1 (1986), pp 91-100, also shows that in the fermentation not all sugar is utilized and that several other organic acids are formed besides lactic acid.

The industrial fermentation to lactic acid requires strict control of temperature and pH. Because of the formation of lactic acid the pH drops during fermentation. A drop in pH below a critical value, depending on the microorganism used in the process, could damage the microorganism's metabolic process and bring the fermentation process to a stop. Therefore, it is common practice to add a neutralizing agent, i.e. a base such as $Ca(OH)_2$, $Mg(OH)_2$, NaOH, KOH or ammonia to the fermentation reaction and thus produce a lactate salt such as calcium lactate, sodium lactate etcetera. Normally both lactic acid and lactate salt are present in the fermentation product, depending on the pH of the fermentation product. The fermentation can be done with conventional lactic acid-producing microorganisms such as bacteria yeasts and fungi, such as lactobacilli, moderately thermophilic bacilli, *Rhizopus* and *Aspergillus*. Preferred are the moderately thermophilic bacilli such as *Bacillus coagulans, Bacillus thermoamylovorans, Geobacillus stearothermophylus* and *Bacillus smithii*, because these types of micro-organisms can ferment at relatively high temperature.

After fermentation, the lactate and lactic acid-containing fermentation product must be separated from the biomass. Said lactic acid-containing fermentation product is in the liquid form (i.e. liquid or in solution). Usually this biomass is separated by means of filtration, centrifuging, flocculation, coagulation, flotation or combinations thereof. After biomass separation, the pH of the fermentation product is decreased by means of acid addition such as sulphuric acid so that lactic acid and a salt of the neutralizing base and the added acid is formed. For example, if calcium hydroxide is used as neutralizing agent, the fermentation product will comprise both lactic acid and calcium lactate. Upon addition of sulphuric acid, lactic acid and calcium sulphate (gypsum) will be formed. The gypsum, or any other salt, is removed and the lactic acid is isolated. The resulting lactic acid can be subjected to further purification steps.

Conventional subsequent purification steps are distillation including short path distillation and vacuum distillation, crystallization, salt SWAP, electrodialysis, extraction (both forward and back-extraction), carbon treatment, ion exchange and combinations thereof. These purification steps can be combined with intermediate concentration steps.

The invention is further illustrated by means of examples which are not to be interpreted as limitative.

EXAMPLE 1

Fermentation to Lactic Acid Using Various Substrates

The fermentability of molasses, thick juice and concentrated raw juice substrates originating from a sugar factory (5 samples with Brix values varying from 59.6 to 73.2, concentrated at temperatures of 55, 60, 75, and 85° C.), was tested in separate fermentations. For all substrates, the following procedure was applied: the substrate was diluted with water to a sucrose concentration of approximately 300 g/l. To this solution, 6.0 g/l nutrients were added and the pH was adjusted to 6.4 using lime. Subsequently, the medium was heated to 54° C. and the fermentation was started with 10% (v/v) of a sucrose-grown inoculum of a lactic acid-producing microorganism. During the fermentation diluted lime was added to keep pH at 6.4 and the temperature was controlled at 54° C.

A fermentation in which white sugar (sucrose) was used as substrate, and otherwise applying the same conditions, was carried out for comparison.

Table 1 summarizes the results of these fermentations. Fermentations based on molasses hardly showed any activity; only a small fraction of the sugar was consumed after 45 hrs and the productivity collapsed to virtually zero. The fermentability of thick juice was more active, but still only a part of the sugar was consumed. Concentrated raw juice could be fermented completely. Compared to the reference sucrose fermentation, the lactic acid yield and byproduct profile (organic acids) is similar; the chiral purity is lower but still acceptable. The residual sugar content is higher, because concentrated raw juice contains some sugars that are not/slowly fermented.

TABLE 1

Summary fermentation results for sucrose (reference), molasses, thick juice and concentrated raw juice.

| | Composition final broth | | | | |
|---|---|---|---|---|---|
| Substrate | Lactate (% w/w of max. obtainable) | Chiral purity lactate (% S) | Residual sugars (% w/w of sugar input) | Polysaccharides (% w/w of lactate formed) | Total organic acids* (% w/w) |
| Sucrose*** | 95% | 99.7% | 1% | 0.9% | n.d. |
| Molasses | n.d. | n.d. | 100% | n.d. | n.d. |
| Thick juice | n.d. | n.d. | >50% | n.d. | n.d. |
| Concentrated raw juice** | 95% | 99.2% | 3.5% | 2.3% | <0.2% |

*Sum of succinic, pyruvic, formic, 2-hydroxybutyric and acetic acid
**Average of 11 fermentations
***Average of 13 fermentations
n.d. = not determined

EXAMPLE 2

Concentrated Raw Sugar Beet Juice in Fermentation on Industrial Scale

Two semi-industrial fermentations (scale 5000 liters) on concentrated raw beet juice were performed. Of the final fermentation broth of these two fermentations biomass was removed and the lactate-containing product was acidulated.

A. Materials and Methods

Substrate

Sugar beets were cut, washed and extracted in water at 70° C. The pulp was eliminated and the raw beet juice was subjected to heat treatment at 60° C., solid/liquid separation and evaporation at 65° C. to make concentrated raw beet juice of a Brix between 65-70.

The density of the batches of concentrated raw beet juice was 1.334 kg/l and 1.335 kg/l at 66 Brix, respectively.

Fermentation

Fermentation of concentrated raw beet juice was carried out in the 5000 l fermenter using a lactic acid-producing microorganism. The medium composition of the fermentation is shown in table 2.

TABLE 2

The 5 m³ reactor received a medium of the following composition:

| Medium composition | added amount |
|---|---|
| Water | 2000 l |
| Concentrated raw beet juice (appr. 70°Bx) | 1000 l |
| Nutrient | 18.16 kg |
| Start volume | 3000 l |
| Inoculum | 500 l |

The temperature during the fermentation was kept at 54° C. The pH was controlled by adding a slurry of lime.

Both fermentations started with 275 g/l sucrose (and a total amount of approximately 3 g/l glucose and fructose).

Biomass Removal

Flocculation, to remove bacterial cells, metals, proteins etc., was performed with sugar free final fermentation broth by alkalizing the broth at a temperature of 75° C. with lime and adding flocculant.

The clear top layer was siphoned off as soon as the settling of the biomass was complete. The clear alkaline top layer was subsequently transferred to a second 5 m³ reactor for acidulation. The biomass containing bottom layer was discarded.

Acidulation

The clear alkaline top layer was continuously stirred and sulphuric acid (96%) was added slowly using a pump. This was continued until a pH of 2.2 and a conductivity of approximately 5 mS was reached. Precipitation of calcium was checked using an ammonium oxalate solution (35.5 g/l). The acidulated broth was removed from the reactor and isolated from the formed gypsum.

The clear crude lactic acid solution was subjected to conventional purification steps to make final S-lactic acid (90%).

Results

Both fermentations performed as expected. The culture followed the growth phase and the stationary or production phase until sugar free. The first fermentation took 24 hours. The second fermentation finished after 21 hours.

Final fermentation broth of the first fermentation had a substantial higher amount of polysaccharides than final fermentation broth of the second fermentation. The difference in the amount of total nitrogen in final fermentation broth from these two batches, is negligible. Optical purity of final fermentation broth was 99.3% for the first fermentation and 99.4% for the second fermentation.

The results of the analyses of final fermentation broth samples are listed in table 3. The results show that concentrated raw sugar beet juice can be fermented to lactic acid on industrial scale.

TABLE 3

Lactate, total residual sugars, polysaccharides and optical purity of final fermentation broth

| 5 m³ final fermentation broth | Lactate (% w/w of max. obtainable) | Total residual sugars (% w/w of input) | Polysaccharides (% w/w of lactate) | Chiral purity (% S-lactate) |
|---|---|---|---|---|
| 1st | 95% | 4.2% | 4.0% | 99.3% |
| 2nd | 95% | 6.5% | 2.6% | 99.4% |

After purification, the resulting lactic acid appeared to fulfill the specifications set for commercial lactic acid for food applications with respect to color, taste and optical purity.

The invention claimed is:

1. A process for preparing lactic acid and/or lactate comprising:
providing a concentrated raw beet juice which has a concentration of at least 60 grams of sucrose per 100 grams of liquid, which means at least a Brix of 60, which has not been subjected to lime addition to a pH of approximately 11.2 and surplus lime addition followed by carbon dioxide addition in two stages with removal of carbonation sludge/lime, optionally diluting the concentrated raw beet juice to a Brix between 16 and 30, and fermenting the concentrated raw beet juice with a lactic acid-producing microorganism to obtain lactic acid and/or lactate.

2. The process according to claim 1 wherein the concentrated raw beet juice has a Brix of at least 70.

3. The process according to claim 1 wherein the concentrated raw beet juice is diluted to a Brix between 16 and 30 prior to fermentation.

4. The process according to claim 1 wherein the microorganism is a moderately thermophilic *Bacillus*.

5. The process according to claim 1 further comprising preparing the concentrated raw beet juice by a process that includes the following steps:
   a) washing and cutting sugar beet to obtain cossettes and extracting the cossettes with water to obtain raw beet juice,
   b) removing beet pulp from the resulting raw beet juice, and
   c) heat treating the raw beet juice at a temperature between 50 and 90 degrees Celsius, and
   d) concentrating the heat treated raw beet juice to at least 60 Brix.

6. The process according to claim 5 wherein step c and step d are combined.

7. The process according to claim 5 wherein prior to step c and/or between step c and d, and/or after step d a liquid/solid separation step is conducted.

8. The process according claim 1 wherein the lactic acid and/or lactate resulting from fermentation is subjected to one or more purification steps.

9. The process according to claim 8 wherein the one or more purification steps comprise biomass separation, extraction, salt swap, distillation, ion exchange, carbon treatment, extraction, and/or concentration and combinations thereof.

* * * * *